United States Patent
Koo et al.

(10) Patent No.: US 9,131,876 B2
(45) Date of Patent: Sep. 15, 2015

(54) PORTABLE SOUND SOURCE PLAYING APPARATUS FOR TESTING HEARING ABILITY AND METHOD OF TESTING HEARING ABILITY USING THE APPARATUS

(75) Inventors: Yoon-seo Koo, Seoul (KR); Dong-wook Kim, Seoul (KR)

(73) Assignee: SAMSUNG ELECTRONICS CO., LTD. (KR)

(*) Notice: Subject to any disclaimer, the term of this patent is extended or adjusted under 35 U.S.C. 154(b) by 803 days.

(21) Appl. No.: 12/853,628

(22) Filed: Aug. 10, 2010

(65) Prior Publication Data
US 2011/0046511 A1    Feb. 24, 2011

(30) Foreign Application Priority Data

Aug. 18, 2009 (KR) .................. 10-2009-0076391
Aug. 10, 2010 (KR) .................. 10-2010-0076761

(51) Int. Cl.
*A61B 5/00* (2006.01)
*A61B 5/12* (2006.01)
*H04R 25/00* (2006.01)

(52) U.S. Cl.
CPC . *A61B 5/121* (2013.01); *A61B 5/12* (2013.01); *A61B 5/123* (2013.01); *H04R 25/70* (2013.01)

(58) Field of Classification Search
CPC .......... A61B 5/12; A61B 5/121; A61B 5/123; H04R 25/70
USPC ............................................ 600/559; 73/585
See application file for complete search history.

(56) References Cited

U.S. PATENT DOCUMENTS

| 7,288,071 | B2 | 10/2007 | Harrison et al. |
| 8,238,591 | B2 * | 8/2012 | Latzel ........................ 381/312 |
| 2006/0045281 | A1 * | 3/2006 | Korneluk et al. ............... 381/60 |
| 2007/0276285 | A1 * | 11/2007 | Burrows et al. ............... 600/559 |

FOREIGN PATENT DOCUMENTS

| JP | 07-066767 A | 3/1995 |
| JP | 08-191340 A | 7/1996 |
| JP | 2000-165483 A | 6/2000 |
| JP | 2004-000490 A | 8/2004 |
| KR | 1020030067849 A | 8/2003 |
| KR | 1020060072555 A | 6/2006 |
| KR | 1020060097404 A | 9/2006 |

OTHER PUBLICATIONS

Henry et al., "A Frequency Importance Function for a New Monosyllabic Word Test", Nov. 1998, The Australian Journal of Audiology, vol. 20 No. 2, pp. 79-86.*
"Hearing Aid Evaluation (Reference #1)" with English Translation, May 25, 2005 pp. 28-29.
"Practical manual of hearing tests" (Reference #2), May 30, 2008 p. 7-3.
"A research regarding the frequency charateristics of the phonemes of Korean" (Reference #3), Feb. 2006 p. 42.
"Levels of Hearing Loss", Provincial Health Services Authority, http://www.phsa.ca/AgenciesAndServices/Services/BCEarlyHearing/ForFamilies/Ass . . . , Mar. 27, 2013 p. 1-2.

* cited by examiner

*Primary Examiner* — Devin Henson
(74) *Attorney, Agent, or Firm* — Cantor Colburn LLP

(57) ABSTRACT

A method of testing a hearing ability of a user using a portable sound source playing apparatus includes; outputting a signal indicating at least one phoneme, obtaining a response of a user regarding a degree of audibility of the output signal, and testing the hearing ability of a user based on hearing characteristics of the user showing the degree of audibility of a frequency band comprising a frequency of the at least one phoneme based on the obtained response.

20 Claims, 6 Drawing Sheets

FIG. 4

| GROUP 1 | | GROUP 2 | | GROUP 3 | | GROUP 4 | |
|---|---|---|---|---|---|---|---|
| 1.귀 | 26.향 | 1.혀 | 26.금 | 1.눈 | 26.흠 | 1.글 | 26.밭 |
| 2.힘 | 27.법 | 2.독 | 27.흉 | 2.공 | 27.귤 | 2.집 | 27.깨 |
| 3.논 | 28.산 | 3.잠 | 28.뇌 | 3.길 | 28.면 | 3.꿈 | 28.연 |
| 4.맛 | 29.골 | 4.복 | 29.역 | 4.옷 | 29.농 | 4.선 | 29.못 |
| 5.솔 | 30.짐 | 5.운 | 30.명 | 5.밥 | 30.삽 | 5.목 | 30.절 |
| 6.잔 | 31.녹 | 6.갓 | 31.쌀 | 6.섬 | 31.무 | 6.앞 | 31.광 |
| 7.국 | 32.끌 | 7.쥔 | 32.범 | 7.돈 | 32.안 | 7.넷 | 32.시 |
| 8.솜 | 33.통 | 8.납 | 33.코 | 8.장 | 33.굿 | 8.벽 | 33.달 |
| 9.닭 | 34.삼 | 9.문 | 34.깃 | 9.극 | 34.틀 | 9.상 | 34.젓 |
| 10.옆 | 35.뽕 | 10.곳 | 35.발 | 10.춤 | 35.떡 | 10.돌 | 35.쌈 |
| 11.불 | 36.되 | 11.숲 | 36.등 | 11.먹 | 36.매 | 11.틈 | 36.묵 |
| 12.남 | 37.폭 | 12.종 | 37.질 | 12.솟 | 37.엿 | 12.겹 | 37.뱀 |
| 13.숫 | 38.설 | 13.답 | 38.더 | 13.방 | 38.죄 | 13.육 | 38.만 |
| 14.감 | 39.뜻 | 14.책 | 39.뜸 | 14.적 | 39.빚 | 14.말 | 39.콩 |
| 15.윷 | 40.명 | 15.땀 | 40.실 | 15.강 | 40.담 | 15.소 | 40.벗 |
| 16.들 | 41.은 | 16.셋 | 41.곽 | 16.손 | 41.시 | 16.검 | 41.쇠 |
| 17.탈 | 42.금 | 17.망 | 42.붓 | 17.막 | 42.뺨 | 17.박 | 42.땅 |
| 18.배 | 43.점 | 18.곁 | 43.맥 | 18.벌 | 43.팔 | 18.뜰 | 43.벗 |
| 19.침 | 44.빛 | 19.일 | 44.일 | 19.끝 | 44.샘 | 19.총 | 44.님 |
| 20.꿀 | 45.싹 | 20.죽 | 45.뼈 | 20.칼 | 45.뚝 | 20.낮 | 45.속 |
| 21.반 | 46.벼 | 21.밤 | 46.살 | 21.숨 | 46.잎 | 21.술 | 46.품 |
| 22.멋 | 47.왕 | 22.신 | 47.몸 | 22.낫 | 47.별 | 22.단 | 47.인 |
| 23.키 | 48.색 | 23.널 | 48.풀 | 23.뒤 | 48.씨 | 23.쥐 | 48.뿔 |
| 24.딸 | 49.물 | 24.새 | 49.봄 | 24.백 | 49.좀 | 24.굴 | 49.해 |
| 25.겁 | 50.개 | 25.꽃 | 50.끈 | 25.꼴 | 50.활 | 25.흙 | 50.곰 |

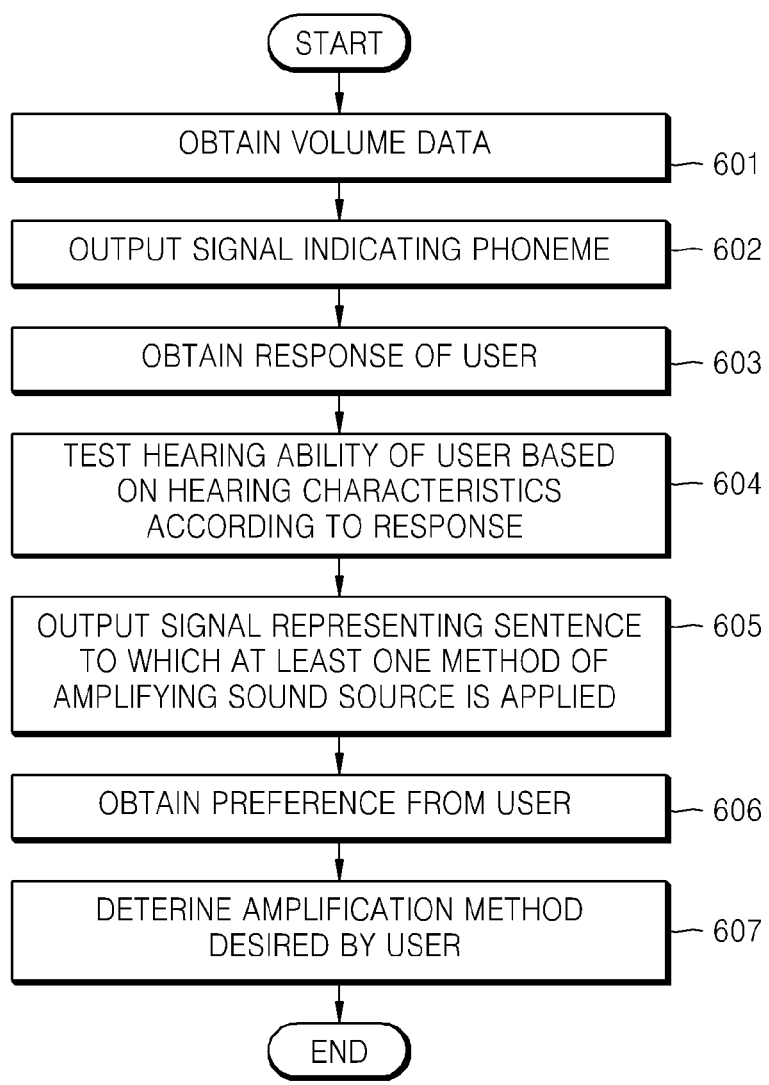

PORTABLE SOUND SOURCE PLAYING APPARATUS FOR TESTING HEARING ABILITY AND METHOD OF TESTING HEARING ABILITY USING THE APPARATUS

CROSS-REFERENCE TO RELATED APPLICATIONS

This application claims priority to Korean Patent Application No. 10-2009-0076391, filed on Aug. 18, 2009, and Korean Patent Application No. 10-2010-0076761, filed on Aug. 10, 2010, and all the benefits accruing therefrom under 35 U.S.C. §119, the contents of which in their entirety are herein incorporated by reference.

BACKGROUND

1. Field

The present disclosure relates to a portable sound source playing apparatus for testing hearing ability and a method of testing the hearing ability using the apparatus.

2. Description of the Related Art

Recently, the number of people who suffer from hearing loss has been increasing due to an increased use of personal audio apparatuses, an increase in the numbers of elderly people, and an increasing number of noisy environments. A hearing test is typically performed by subjecting a user to a sound, e.g., a pure tone wherein a frequency and amplitude thereof may vary and observing the reaction of the user to the tone.

SUMMARY

Provided are portable sound source playing apparatuses for testing hearing ability, and methods of testing hearing ability in portable sound source playing apparatuses.

Also provided are computer readable recording media for executing the methods.

Additional aspects will be set forth in part in the description which follows and, in part, will be apparent from the description, or may be learned by practice of the presented embodiments.

According to an aspect of the present disclosure, a method of testing a hearing ability of a user in a portable sound source playing apparatus includes; outputting a signal indicating at least one phoneme, obtaining a response of the user regarding a degree of audibility of the output signal, and testing the hearing ability of the user based on hearing characteristics of the user showing the degree of audibility of a frequency band comprising a frequency of the at least one phoneme based on the obtained response.

According to another aspect of the present disclosure, there is provided a computer readable recording medium having embodied thereon a program for executing the above-described method.

According to another aspect of the present disclosure, a sound source playing apparatus includes; an output unit which outputs a signal indicating at least one phoneme, a user interface unit through which a response of a user regarding the degree of audibility of the output signal is input, and a processor which tests the hearing ability of the user based on hearing characteristics of the user indicating the degree of audibility regarding a frequency band comprising a frequency of the at least phoneme according to the input response.

BRIEF DESCRIPTION OF THE DRAWINGS

These and/or other aspects will become apparent and more readily appreciated from the following description of the embodiments, taken in conjunction with the accompanying drawings of which:

FIG. 4 illustrates examples of phonetically balanced words;

FIG. 6 is a flowchart illustrating an embodiment of a method of testing the hearing ability of a user using a sound source playing apparatus, according to the present disclosure.

DETAILED DESCRIPTION

Figure 1:
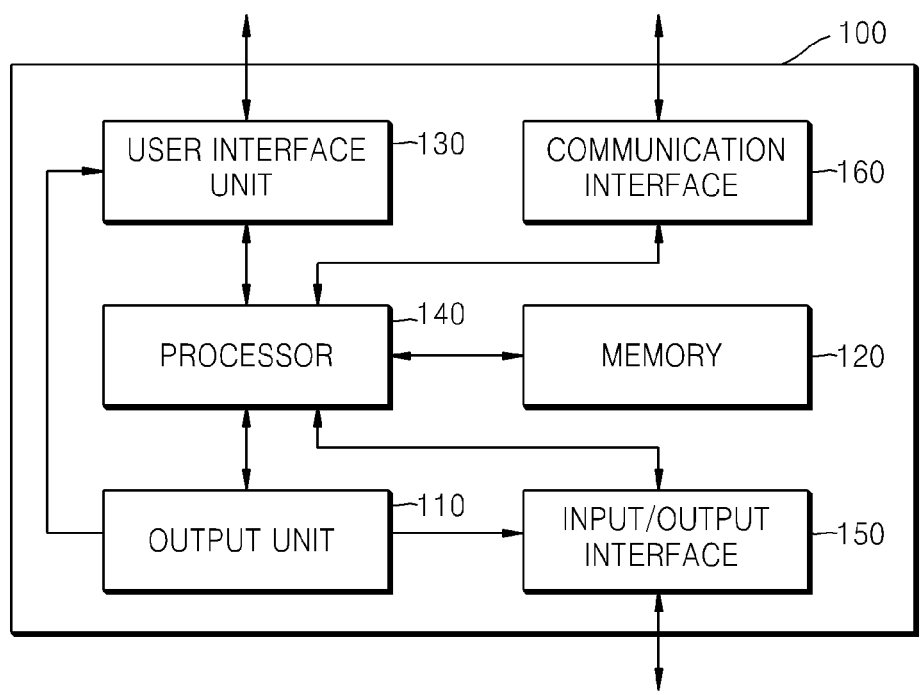
FIG. 1 is a block diagram illustrating an embodiment of a sound source playing apparatus according to the present disclosure.

Embodiments now will be described more fully hereinafter with reference to the accompanying drawings, in which embodiments are shown. These embodiments may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the disclosure.

All methods described herein can be performed in a suitable order unless otherwise indicated herein or otherwise clearly contradicted by context. The use of any and all examples, or exemplary language (e.g., "such as"), is intended merely to better illustrate the disclosure and does not pose a limitation on the scope thereof unless otherwise claimed. No language in the specification should be construed as indicating any non-claimed element as essential to the practice of the embodiments as used herein.

Hereinafter, the embodiments will be described in detail with reference to the accompanying drawings.

FIG. 1 is a block diagram illustrating an embodiment of a sound source playing apparatus 100 according to the present disclosure. Referring to FIG. 1, the present embodiment of a sound source playing apparatus includes an output unit 110, a memory 120, a user interface unit 130, a processor 140, an input/output interface 150, and a communication interface 160. Here, description will focus on units of the sound source playing apparatus 100 that test the hearing ability of a user, display results of the hearing test or play sound sources by applying the test results. Accordingly, it will be understood to one of ordinary skill in the art that the sound source playing apparatus 100 may also include other general elements as would be known to one of ordinary skill in the art.

The sound source playing apparatus 100 is a portable apparatus that can be carried by a user whose hearing ability is to be tested, and is an apparatus that plays a sound source or outputs a signal for playing a sound source. As used herein, the term "portable" means that the sound source playing apparatus 100 can be conveniently carried by hand or worn on the body of a user. Also, the term "sound source playing apparatus" refers to an apparatus that generates an audible sound from data that is stored as a digital signal or an analog signal, or that generates a signal for generating an audible sound.

Examples of the sound source playing apparatus 100 are a mobile phone, a personal digital assistance ("PDA") terminal, an MPEG audio layer-3 ("MP3") player, a compact disc ("CD") player, a portable media player, etc., but are not limited thereto. In this regard, the sound source playing apparatus 100 may be any type of apparatus that generates an audible sound or outputs a signal for generating an audible sound.

The sound source playing apparatus 100 is an apparatus that generates an audible sound or that outputs a signal for generating an audible sound and additionally includes a function of testing the hearing ability of a user. As used herein, the term "hearing ability" refers to the capability of hearing a sound through the ears or auditory nerve of a user, and a hearing test refers to a test that measures the degree of audibility of a particular sound or range of sounds. That is, the sound source playing apparatus 100 refers to an apparatus playing a sound source or outputting a signal for playing a sound source, to which a function of measuring the degree of audibility through the ears is added.

A signal for playing a sound source is a signal for generating a sound. That is, the output unit 110 outputs a signal for generating a sound. The signal for generating a sound is a waveform having amplitude, frequency and phase. The signal is transformed into a sound by being amplified using an amplifier to generate a sound, or by another sound source playing apparatus such as an earphone that is connected to the sound source playing apparatus 100 via the input/output interface 150. The sound source playing apparatus 100 may test the hearing ability of the user with reference to the degree of audibility at which the user hears the sound generated in the above-described manner.

The output unit 110 outputs a signal that indicates at least one phoneme. The at least one phoneme may be a syllable or a speech sound (e.g., a sound typically made via a voice). Accordingly, the output unit 110 may output a signal that indicates at least one syllable, and also, the output unit 110 may output a signal that indicates at least one speech sound.

For example, the syllable is formed of at least one phoneme. Also, the speech sound is formed of at least one syllable; for example, a monosyllable consists of one syllable, a disyllable consists of two syllables, and a trisyllable consists of three syllables, and in this manner, a speech sound consisting of a plurality of syllables may be expressed. A syllable is a term from the field of phonetics that refers to a smallest unit of pronunciation. For example, in the Korean language, a syllable consists of a phoneme or phonemes such as a consonant-vowel-consonant combination (e.g., 휘 consists of ㅎ, ㅣ, and ㅟ), or a consonant-vowel (e.g., 기 consists of ㄱ and ㅣ), or a vowel (e.g., 아 consists of ㅏ).

The user may generate a sound that a signal output from the output unit 110 expresses by manipulating the user interface unit 130 of the sound source playing apparatus 100. The sound generated by playing the signal output from the sound source playing apparatus 100 stimulates an auditory organ of the user so as to allow the user to hear the sound. The output unit 110 outputs an audio signal for generating sound, and the user interface unit 130 (e.g., speaker) may directly generate a sound in the sound source playing apparatus 100 using the output audio signal. In order that a sound is generated in another sound source playing apparatus (e.g., ear phone, Bluetooth ear phone, speaker, etc.) connected to the sound source playing apparatus 100, the input/output interface unit 150 transmits an audio signal to the additional sound source playing apparatus. In such an embodiment, the sound expressed by the output signal is generated by the additional sound source playing apparatus.

As described above, the output unit 110 is configured such that a sound is directly generated in the sound source playing apparatus 100 through the user interface unit 130 or such that a sound is generated by another sound source playing apparatus that is connected to the sound source playing apparatus 100 via the input/output interface 150. A signal output from the output unit 110 may be generated by the processor 140 based on data read from the memory 120. Embodiments also include configurations wherein the output unit 110 may be included in the processor 140 or may be an independent chip separate from the processor 140.

At least one phoneme group classified according to peak frequencies of phonemes of the respective phonemes in the phoneme groups is stored in the memory 120. Also, groups of syllables classified according to peak frequencies of phonemes of the syllables may be stored in the memory 120.

The groups of the phonemes or the groups of the syllables include phonemes or syllables included in a plurality of frequency bands within an audible frequency range. The audible frequency range refers to a frequency range of sound waves that can be heard by human ears, which is a range from about 15 Hz to about 20 KHz. That is, the audible frequency range is divided into a plurality of frequency bands, and syllables consisting of phonemes with peak frequencies included in the divided frequency bands may be grouped therein.

In the present embodiment, the memory 120 is a general storage medium that may be well known to those of ordinary skill in the art. Examples of the memory 120 include a hard disk drive ("HDD"), a read only memory ("ROM"), a random access memory ("RAM"), a flash memory, and a memory card.

As described above, a syllable refers to the smallest unit of pronunciation of a language, and one syllable consists of at least one phoneme. As used in the field of phonetics, a phoneme refers to the phonological smallest unit in phonology. That is, a phoneme is the smallest unit of sound that distinguishes between meaningful utterances of speech. In the Korean language, there are phonemes such as, /아/, /어/, /우/, /오/, /이/, /에/, /ㄴ/, /ㅁ/, /ㄹ/, /ㅣ/, /ㄲ/, /ㅋ/, /ㅂ/, /ㅃ/, /ㅍ/, /ㅎ/, /ㄷ/, /ㄸ/, /ㅌ/, /ㅈ/, /ㅉ/, /ㅊ/, /ㅅ/, /ㅆ/, etc.

Figure 2:
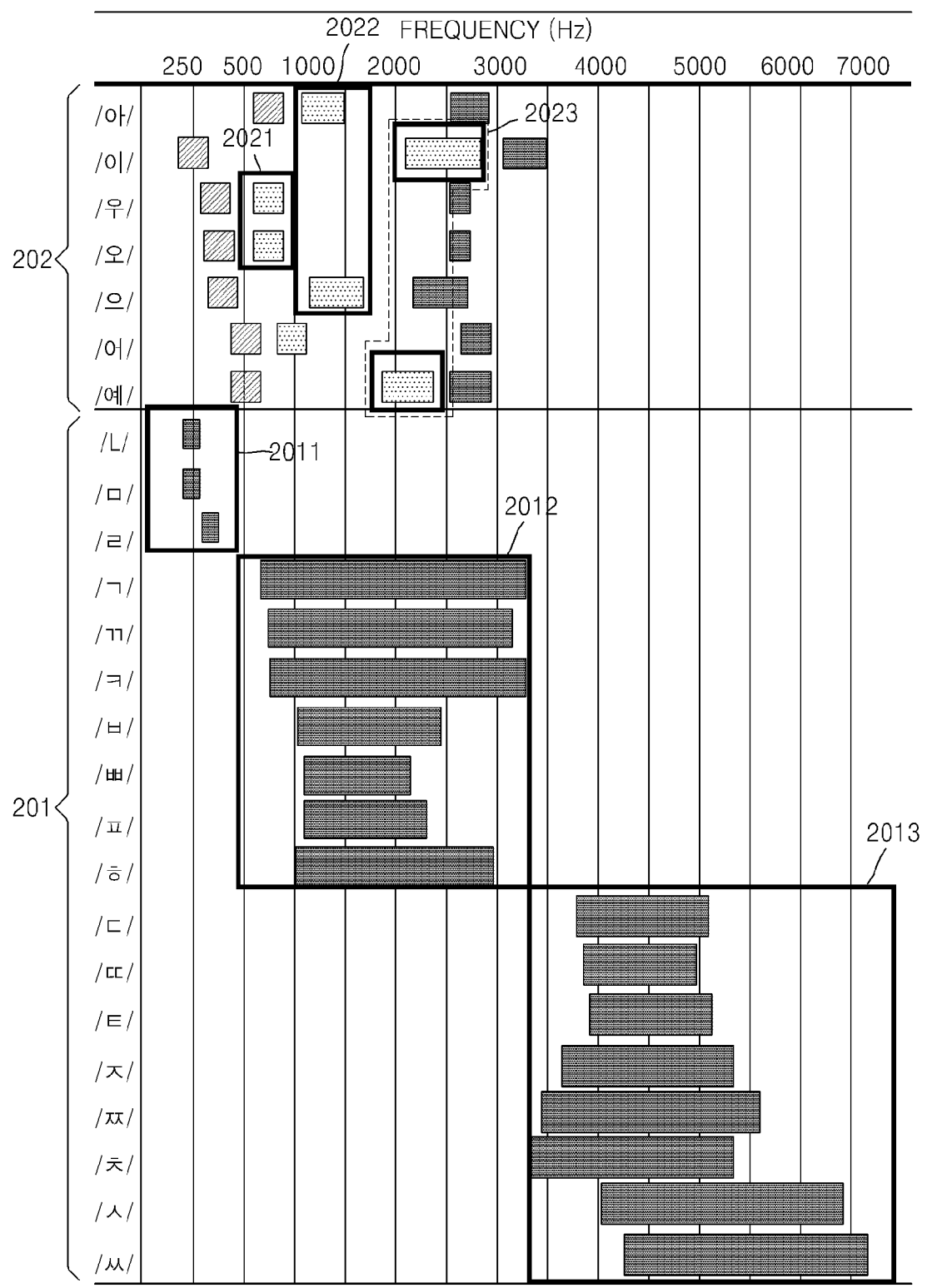
FIG. 2 illustrates frequency characteristics of phonemes of the Korean language.

FIG. 2 illustrates the frequency characteristics of phonemes of the Korean language. Referring to FIG. 2, frequency ranges of the phonemes of the Korean language that are classified as consonants and vowels are illustrated. In this regard, the consonants and the vowels are divided into a plurality of groups according to the peak frequency ranges thereof.

Referring to FIG. 2, a consonant list 201 indicates a frequency range of consonants that are divided into three groups according to their respective frequency range. Group 1 (2011) refers to consonants of a frequency range between about 250 Hz and less than 500 Hz, and Group 2 (2012) refers to consonants of a frequency range between about 650 Hz and less than 3000 Hz, and Group 3 (2013) refers to consonants of a frequency range between about 3000 Hz and less than 7000 Hz.

Consonants such as /ㄴ/, /ㅁ/, /ㄹ/ are included in Group 1 (2011), consonants such as /ㄱ/, /ㄲ/, /ㅋ/, /ㅂ/, /ㅃ/, /ㅍ/, /ㅎ/ are included in Group 2 (2012), and consonants such as /ㄷ/, /ㄸ/, /ㅌ/, /ㅈ/, /ㅉ/, /ㅊ/, /ㅅ/, /ㅆ/ are included in Group 3.

Also, a vowel list 202 indicates a frequency range of vowels. Referring to the vowel list 202, a single vowel consists of three formant frequencies. A formant frequency refers to a peak frequency having higher energy in a frequency spectrum that is represented by integrating along a frequency axis according to amplitude of sound versus time of the vowel. Referring to the vowel list 202, three formant frequencies constituting one vowel may be respectively indicated by, starting from a lowest frequency band, a first formant, a second formant, and a third formant. As illustrated in the vowel list 202, since the frequency bands of vowels of the first formant and the third formant are similar across all vowels, vowels may be classified into three groups of vowels according to a frequency band of the second formant band. Vowels of a frequency range between about 600 Hz and less than 800 Hz are included in Group 2-1 (2021), vowels of a frequency range between about 1000 Hz and less than 1300 Hz are included in Group 2-2 (2022), vowels of a frequency range between about 2000 Hz and less than 3000 Hz are included in Group 2-3 (2023).

In Group 2-1 (2021), vowels such as /우/, /오/, etc. are included, in Group 2-2 (2022), vowels such as /아/, /어/, etc. are included, and in Group 2-3 (2023), vowels such as /이/, /에/, etc. are included.

Referring to FIG. 2, if, according to a result of the hearing test of a user, the degree of audibility of the consonants of Group 3 (2023) is low, and also, if the user does not distinguish between the vowels /우/ and /아/ or between the vowels /오/ and /어/, it may be determined that the user has a hearing loss regarding the frequency band between about 1000 Hz and less than 1300 Hz which is the frequency band of Group 2-2 (2022) and the frequency band between about 2000 Hz and less than 3000 Hz which is the frequency band of Group 3 (2023).

FIG. 2 illustrates the frequency characteristics of phonemes of the Korean language, but the frequency characteristics of phonemes may also be applied to other languages.

Figure 3:
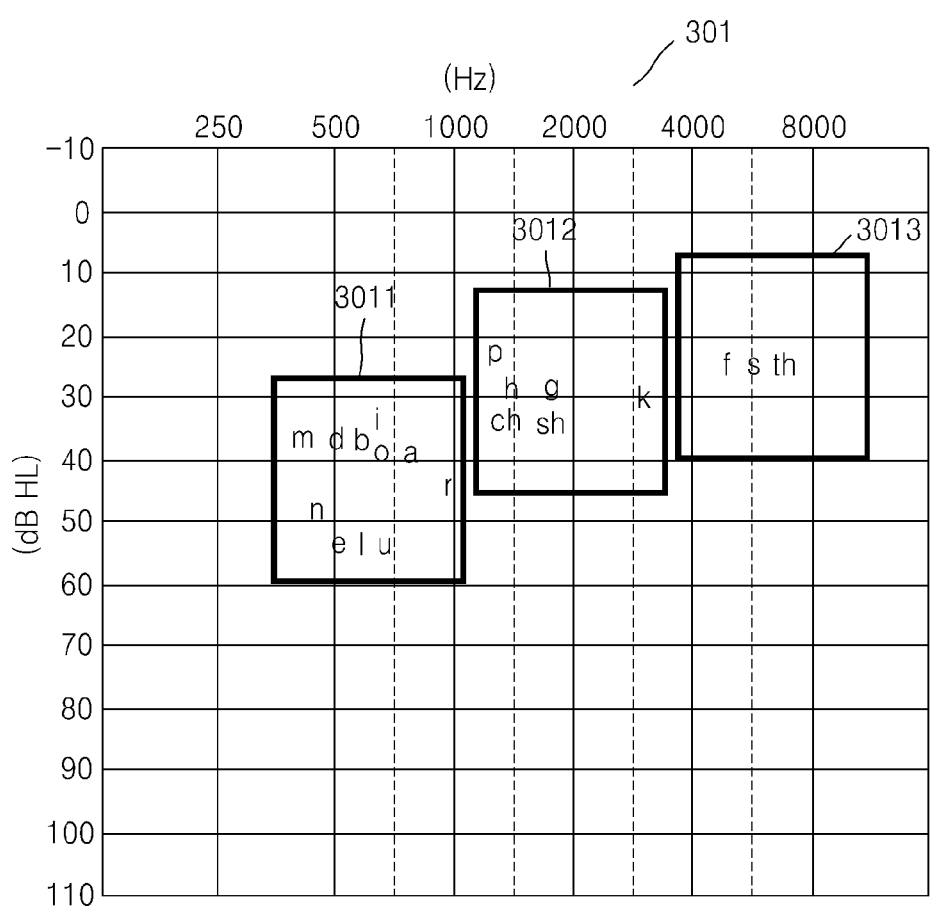
FIG. 3 illustrates frequency characteristics of phonemes of the English language.

FIG. 3 illustrates the frequency characteristics of phonemes of the English language. Referring to FIG. 3, the frequency ranges of phonemes of the English language are illustrated, and the phonemes are divided into a plurality of groups according to the frequency range.

Referring to FIG. 3, a phoneme list 301 indicates a frequency range of phonemes, and the phonemes are divided into three groups according to the frequency ranges thereof. Group 1 (3011) refers to phonemes in a frequency range between about 300 Hz and less than 1200 Hz, Group 2 (3012) refers to phonemes in a frequency range between about 1200 Hz and less than 4000 Hz, and Group 3 (3013) refers to phonemes in a frequency range between about 4000 Hz and less than 8000 Hz.

Phonemes such as /m/, /d/, /b/, /i/, /o/, /a/, /n/, /e/, /l/, /u/, /r/, are included in Group 1 (3011), phonemes such as /p/, /h/, /g/, /k/, /ch/, /sh/ are included in Group 2 (3012), and phonemes such as /f/, /s/, /th/ are included in Group 3 (3013).

Accordingly, the hearing characteristics of a user may be determined according to the result of the hearing test with respect to the frequency characteristics of phonemes of the Korean and English languages respectively illustrated in FIGS. 2 and 3.

Referring to FIG. 1 again, groups of at least one phoneme or groups of syllables classified according to the peak frequencies of phonemes of the syllables are stored in the memory 120. The phonemes or syllables of the groups may be extracted from "phonetically balanced words." As used herein, the term "phonetically balanced word" refers to a group of syllables including a range of phonemes that are overall balanced due to similar sound pressures generated when pronouncing the syllables; that is, a phonetically balanced word includes a wide frequency of sounds.

FIG. 4 illustrates examples of the phonetically balanced words. Referring to FIG. 4, a phonetically balanced word list 401 includes four groups respectively including syllables having equivalent speech discrimination. In the phonetically balanced word list 401, monosyllables are included in each of Group 1 (4011), Group 2 (4012), Group 3 (4013), and Group 4 (4014). The phonetically balanced word list 401 includes examples of groups of syllables including phonemes that are balanced overall due to similar sound pressures generated when pronouncing the syllables. The sound source playing apparatus 100 may test the hearing ability of a user using not only the phonetically balanced word list 401 but also using other lists (not shown) of syllables including phonemes that are balanced overall due to similar sound pressures generated when pronouncing the syllables.

Referring to FIG. 1 again, the phonetically balanced word list 401 illustrated in FIG. 4 is stored in the memory 120. Also, groups of syllables classified according to peak frequencies of phonemes of the syllables may be stored in the memory 120. The syllables of the group may be extracted from the phonetically balanced word list 401 but are not limited thereto.

Also, the groups of at least one phoneme classified according to frequencies of phonemes may be stored in the memory 120.

The output unit 110 reads at least one phoneme or syllable stored in the memory 120, and outputs a signal indicating the read phoneme or syllable. For example, assuming that the phonetically balanced word list 401 illustrated in FIG. 4 is stored in the memory 120, the output unit 110 outputs a signal indicating a plurality of syllables that are randomly extracted among the syllables of the phonetically balanced word list 401 stored in the memory 120. Alternative embodiments include configurations wherein at least one syllable is extracted from each of the groups of syllables classified according to peak frequencies of phonemes constituting the syllables among the syllables of the phonetically balanced word list 401, and a signal indicating the extracted syllable is output. The hearing characteristics of the user may be determined by observing a reaction(s) of the user to sound generated by the output signal.

For example, if response accuracy of the user to the syllables included in the group of the range between about 1000 Hz and less than 1300 Hz is 20% or less, it may be determined that the degree of audibility of the user is low regarding the above frequency band. Also, an amplification gain regarding the frequency band corresponding to the group may be set to, for example, about 40 dB, to compensate for a signal for playing a sound source. Alternatively, a result of the hearing test showing the hearing characteristics of the user may be displayed to the user using the user interface unit 130. For example, a sentence such as "You have difficulty hearing a high frequency sound", may be displayed to the user through the user interface unit 130, or a graph showing the degree of hearing loss of the user with respect to the frequency may be displayed. Accordingly, the sound source playing apparatus 100 may conveniently determine the hearing characteristics of the user and the sound source playing apparatus 100 may correct the output sound according to the hearing characteristics of the user.

The output signal is played as a sound via the user interface unit 130 or the input/output interface 150. The sound source playing apparatus 100 illustrated in FIG. 1 may test the hearing ability of the user with respect to a plurality of frequency bands using at least one phoneme or syllable through a single test, and thus time for measuring the reaction of the user may be reduced compared to the method of measuring the hearing ability of the user using a pure tone as in a comparative device, and also, the present embodiment may generate an increase in a reliability of the test over the comparative test, where not uniform pure tones may decrease reliability.

The hearing ability may also be tested using a speech sound that is familiar to the user, but a conventional hearing ability test using a speech sound takes a lot of time and the user typically has to visit a particular location for conducting the test. Thus, by comparison, it is convenient to test the hearing ability using the portable sound source playing apparatus 100 according to the current embodiment of the present disclosure.

A response of the user showing the degree of audibility of the sound that is produced by the signal output by the output unit 110 is input to the user interface unit 130. The user interface unit 130 included in the sound source playing apparatus 100 receives an input signal from the user, and displays output information to the user. For example, the user interface unit 130 includes all input/output devices included in the sound source playing apparatus 100, such as a display panel, a mouse, a keyboard, an input button, a touch screen, a liquid crystal display ("LCD") screen, a monitor, and various other devices. Accordingly, the user interface unit 130 may display a result of the hearing test of the user showing the hearing characteristics of the user, and receive volume data from the user. Also, the sound source playing apparatus 100 may obtain a response of the user to a sound representing the signal output by the output unit 110 by recognizing the voice of the user or receiving an input signal input by the user.

The user hears a sound generated by the output unit 110 and inputs a response showing the degree of audibility via the user interface unit 130. For example, a sound generated by a syllable "힘" is played using the sound source playing apparatus 100, and a response indicating whether the user has heard the sound representing the syllable as "힘" is input via the user interface unit 130. Here, the degree of audibility refers to how well the user has heard the sound. Accordingly, the degree of audibility according to the current embodiment of the present invention may indicate how accurately the user has heard a sound represented by syllables generated by the sound source playing apparatus 100 as the sound of the syllables.

For another example, a phoneme "ㄴ" is played by the sound source playing apparatus 100, and the user inputs a response about whether the user has heard a sound indicated by the phoneme as "ㄴ" via the user interface unit 130. Accordingly, the degree of audibility according to the current embodiment of the present invention may indicate whether the user has heard the sound represented by the above phoneme.

For another example, a phoneme "b" is played by the sound source playing apparatus 100, and the user inputs a response about whether the user has heard a sound indicated by the phoneme as "b" via the user interface unit 130. Accordingly, the degree of audibility according to the current embodiment of the present invention may indicate whether the user has heard the sound represented by the above phoneme.

The user interface unit 130 may obtain a response regarding the degree of audibility from the user through various user interfaces. For example, in order to measure the degree of comprehension regarding phonemes or syllables, the user may directly input the phoneme or the syllable he/she has heard. Then, it is determined whether the input syllable from the user is the same as the phoneme or the syllable played by the sound source playing apparatus 100 so as to measure the degree of audibility of the user. Alternative embodiments include configurations wherein the degree of audibility of the user may be measured as the user selects one phoneme or syllable corresponding to the phoneme or syllable played by the sound source playing apparatus 100 among the examples of the plurality of the syllables. Alternative embodiments also include configurations wherein the user may answer "Yes" or "No" regarding whether he/she has heard the phoneme or the syllable.

The above-described methods are examples for obtaining a response showing the degree of audibility of the user from the user using the sound source playing apparatus 100, but the present disclosure is not limited thereto, and other various methods are also possible.

The processor 140 controls the overall functions of the sound source playing apparatus 100.

The processor 140 controls the output unit 110, the memory 120, the user interface unit 130, the input/output interface 150, and the communication interface 160. The processor 140 tests the hearing ability of the user based on the hearing characteristics representing the degree of audibility regarding a frequency band including a frequency of a syllable, according to the response input by the user. That is, the processor 140 tests the hearing ability of a user using the method described above.

For example, the processor 140 allows a signal indicating at least one phoneme or syllable to be output by the output unit 110, and the user hears a sound that is generated by the output signal and inputs a response showing the degree of audibility of the sound via the user interface unit 130. The processor 140 determines the hearing characteristics of the user with reference to the input response.

As described above, the user inputs a response showing the degree of audibility of a plurality of phonemes or syllables via the user interface unit 130, and the processor 140 analyzes the input response to determine the hearing ability of the user representing the degree of audibility of a frequency of a sound source. That is, the processor 140 determines the hearing characteristics regarding the frequency band including a peak frequency of a phoneme or a syllable constituting a syllable, with reference to the response of the user. For example, if the user shows a low degree of audibility regarding phonemes or syllables included in a frequency band between about 600 Hz and less than 800 Hz, that is, if the accuracy of the response of the user to the phoneme or syllables included in the above frequency band is low, it may be determined that the user has difficulty in hearing the frequency band between about 600 Hz and less than 800 Hz. Thus, the hearing test of the user may be conducted by determining the hearing characteristics of the user based on a result of the determination.

Also, the processor 140 corrects a signal for playing a sound source by applying the hearing characteristics of the user to the signal. The processor 140 increases a gain (amplitude) of a frequency range where the user has difficulty in hearing, by reflecting the hearing characteristics of the user to the sound source playing apparatus 100, thereby performing correction by compensating for the signal for playing a sound source. The corrected signal is output by the output unit 110 and the user may hear a sound representing the corrected signal. Also, the processor 140 adjusts an amplification gain regarding a frequency of a sound source according to the hearing characteristics of the user to calculate algorithms for adjusting an output signal. The algorithms refer to all kinds of methods used for converting between electrical signals and sound signals; for example, a codec may be used as one of the algorithms. The memory 120 stores the calculated algorithms and the sound source playing apparatus 100 may read the stored algorithms to reproduce a sound source.

That is, the processor 140 stores algorithms for correcting a signal for playing a sound source in the memory 120 according to the result of the hearing test of the user, and applies the algorithms for correcting a signal for generating a sound source to all sound sources that are to be played using the sound source playing apparatus 100, to allow the sound source to be played. That is, the processor 140 may correct all outputs from the sound source playing apparatus 100 to have the corrected signal, such that the audibility of all sounds from the sound source playing apparatus 100 are tailored for maximum audibility of the user.

When using conventional testing methods involving a hearing testing apparatus, it is difficult to reflect the test results in the sound source playing apparatus 100. However, using the present embodiment of a sound source playing apparatus 100, a hearing ability test may be performed and the test result may be immediately reflected in the sound source playing apparatus 100. Accordingly, a hearing ability test may be performed in the sound source playing apparatus 100, and then the test result may be immediately reflected in the sound source playing apparatus 100 so that the test result is reflected in all sound sources that are to be played later using the portable sound source playing apparatus 100.

Figure 5:
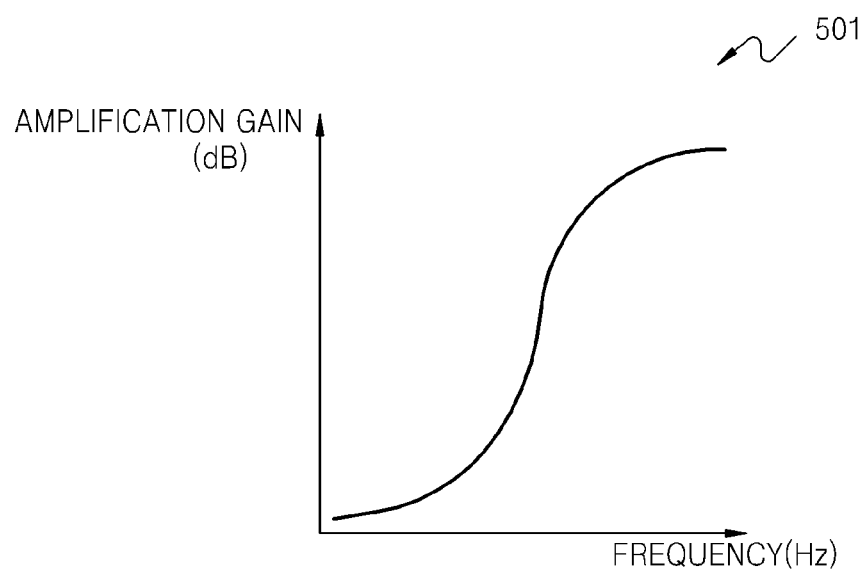
FIG. 5 is a graph illustrating an embodiment of amplification gain with respect to frequency, according to the present disclosure.

FIG. 5 is a graph 501 illustrating an embodiment of an amplification gain with respect to frequency, according to the present disclosure. In the graph 501 of FIG. 5, variation in the amplification gain as a signal moves from a low frequency band to a high frequency band is illustrated. The graph 501 shows the amplification gain with respect to frequency of a user who has difficulty in hearing a high frequency band. That is, an amplification gain for a sound of a low frequency band is reduced and an amplification gain for a sound of a high frequency band is increased so that the user may hear the sound of the high frequency band, which he/she has difficulty in hearing, at a louder volume.

Referring to FIG. 1 again, the processor 140 calculates algorithms for correcting a signal for playing a sound source by applying the hearing characteristics of the user and stores the calculated algorithms in the memory 120. The algorithms refer to the amplification gain regarding a frequency of a signal similar to the graph 501 illustrated in FIG. 5. The processor 140 changes the characteristics of an amplification gain regarding a frequency which is stored as a basic setup or generates a new graph of an amplification gain regarding a frequency according to the hearing characteristics of the user and stores the same in the memory 120.

For example, if the degree of audibility of phonemes or syllables in a frequency range between about 2000 Hz and less than about 3000 Hz is low to the user, the processor 140 calculates algorithms that set an amplification gain of a signal to about 40 dB at a frequency between about 2000 Hz and less than about 3000 Hz. Here, it may be obvious to one of ordinary skill in the art that the above method is an example of algorithms for correcting a signal played as a sound source. Accordingly, the method of correcting a signal played as a sound source is not limited thereto, and other various methods according to the hearing characteristics of the user are possible.

In order that a signal output from the output unit 110 is played by another sound source playing apparatus, the input/output interface 150 functions as an interface that connects the sound source playing apparatus 100 to the other sound source playing apparatus that is connected to the sound source playing apparatus 100. That is, the input/output interface 150 transmits a signal output from the output unit 110 to the other sound source playing apparatus that is connected to the sound source playing apparatus 100, and the other sound source playing apparatus plays a sound representing the signal. For example, the input/output interface 150 may be a head set jack or a universal serial bus ("USB") module provided in an MP3 player or a mobile phone corresponding to the sound source playing apparatus 100.

In a hearing test, the hearing ability normally needs to be conducted for both left and right ears, and thus another sound source playing apparatus for conducting the hearing test for both ears, such as ear phones, is typically used. Accordingly, the input/output interface 150 is connected to the sound source playing apparatus 100 and may function as an interface to all kinds of accessories for playing a sound representing a signal generated by the sound source playing apparatus 100.

Data is transmitted or received between the sound source playing apparatus 100 and external devices via the communication interface 160. According to the user environment, the sound source playing apparatus 100 may not include the communication interface 160.

In the embodiment wherein the sound source playing apparatus 100 is a mobile phone, general functions of the mobile phone such as phone calls, transmission and reception of text messages, internet, etc. may be performed by transmitting or receiving data via the communication interface 160.

Accordingly, the user may easily perform a hearing test using the sound source playing apparatus 100 and immediately obtain a result of the hearing test. Also, by immediately applying the result of the hearing test to the portable sound source playing apparatus 100, the degree to which the user hears the speech sound may be increased by immediately using the result of the hearing test.

Also, the sound source playing apparatus 100 receives volume data from the user via the user interface unit 130, and tests the hearing ability of the user using a signal indicating at least one phoneme or syllable within a set volume based on the received volume data. That is, the sound source playing apparatus 100 receives desired volume data of the user, via the user interface unit 130, and determines the hearing characteristics of the user using a signal indicating at least one phoneme or syllable at the volume set based on the received volume data. The desired volume data of the user refers to a magnitude of a sound pressure with which the user feels most comfortable, which is referred to as a "Most Comfortable Level", and the user sets the volume of the portable sound source playing apparatus using the user interface unit 130.

Since the user may carry the portable sound source playing apparatus 100 and reproduce a sound source anytime, a desired volume of the user may be set in advance in the sound source playing apparatus 100. Alternatively, by determining the volume desired by the user, the sound source playing apparatus 100 may conduct a hearing test using the desired volume of the user.

Alternatively, the sound source playing apparatus 100 may output a signal representing a sentence to which at least one method of amplifying a sound source is applied via the output unit 110, and the user may input a preference for the sentence that represents the signal and is played via the user interface unit 130. The processor 140 may then determine a method of amplifying a sound source desired by the user with reference to the obtained preference of the user. Here, the method of amplifying a sound source refers to varying the time at which compression starts.

That is, if the degree of audibility of a predetermined frequency band of the user is low, the user has a low degree of audibility of hearing a sound with respect to the frequency band, and therefore the time allowed for comprehension of the sound by the user, also referred to as a time analytical ability, is also decreased. A sound of a low frequency band having high energy (e.g., high amplitude) masks a low sound that is emitted before and/or after the sound having high energy. Accordingly, the low sound may be made louder where there is the loud sound by quickly increasing a gain of the low sound and quickly reducing a gain of the loud sound. In one embodiment, the method of amplifying a sound source is a non-linear method, with which speech discrimination may be improved.

Also, embodiments include configurations where in the method of amplifying a sound source, a sound source may be linearly amplified according to the amplitude of a sound source, and if the sound source reaches a predetermined amplitude, the amplitude of the sound source may be compressed. This is to prevent a sound of a sound source from becoming too loud, and the predetermined amplitude may be set arbitrarily. In the non-linear amplification system, when the amplitude of the input sound source changes from a low sound to a sound having a predetermined energy or greater, a loud sound is output while gradually reducing in loudness due to the compression. After a predetermined period of time, the output of the loud sound is stabilized, and this period of time required to reach this stable state is referred to as an attack time. A sound source may be amplified by applying different compression times to different portions of the signal depending upon their frequency and amplitude.

Accordingly, the sound source playing apparatus 100 outputs signals indicating sentences to which the method of amplifying a sound source including varying compression times with respect to the sentences is applied, and the user hears the output sentences and selects a sentence the user determines as optimum. The sentences to which the method of amplifying at least one sound source is applied may be stored in the memory 120 or a sentence to which at least one method of amplifying a sound source is applied may be generated by the processor 140. The processor 140 determines a method of amplifying a sound source desired by the user according to a selection of the user, and may correct a signal for playing the sound source using the determined amplifying method. Also, regarding the algorithms for correcting an output signal, the algorithms may be calculated by applying not only the hearing characteristics of the user but also the above-described method of amplifying a sound source, and may store the calculated algorithms in the memory 120.

Accordingly, the sound source playing apparatus 100 may test the hearing ability of the user while being carried by the user, display a result of the hearing test, and reflect the hearing characteristics of the user in the sound source played by the sound source playing apparatus 100 by applying the result of the hearing test. Accordingly, the user may easily hear a corrected sound source to which the hearing characteristics of the user are applied, without any additional equipment for correcting the hearing ability.

FIG. 6 is a flowchart illustrating an embodiment of a method of testing the hearing ability of a user using the sound source playing apparatus 100, according to the present disclosure. Referring to FIG. 6, the method of testing the hearing ability of a user includes operations that are time-sequentially processed in the sound source playing apparatus 100 illustrated in FIG. 1. Thus, the description regarding the sound source playing apparatus 100 provided above applies to the method of testing the hearing ability according to the present embodiment.

In operation 601, the user interface unit 130 receives volume data from the user. That is, the user inputs volume data regarding a sound pressure with which the user feels most comfortable, which is referred to as a "Most Comfortable Level". The user may input desired volume data using a volume setting button of the user interface unit 130.

In operation 602, the output unit 110 outputs a signal indicating at least one phoneme. Embodiments include configurations wherein the output signal may be played as a sound via the user interface unit 130 or by another sound source playing apparatus via the input/output interface 150.

In operation 603, the user interface unit 130 receives a response of the user regarding the degree of audibility of the output signal. The user interface unit 130 may utilize any method such as a method of pressing a button or a method of inputting a response using the voice of the user among a variety of other input methods as would be known to one of ordinary skill in the art.

In operation 604, the processor 140 tests the hearing ability of the user based on hearing characteristics showing the degree of audibility of the user regarding a frequency band including a frequency of the at least one phoneme, according to the response obtained from the user. Here, a signal for playing a sound source may be corrected by applying the hearing characteristics of the user to the sound source playing apparatus 100. Also, the result of the hearing test of the user based on the hearing characteristics of the user may be displayed on the user interface unit 130.

In operation 605, the output unit 110 outputs a signal representing a sentence to which at least one method of amplifying a sound source has been applied. The at least one method of amplifying a sound source refers to a various time point where compression starts.

In operation 606, the user interface unit 130 obtains a preference of the user regarding the sentence represented by the signal. The preference may be obtained using various methods as described above with reference to operation 603.

In operation 607, the processor 140 determines an amplification method that is desired by the user with reference to the obtained preference of the user. The determined desired amplification method of the user may be applied to the sound source playing apparatus 100.

Embodiments include configurations wherein operations 602 through 604 may be repeated a plurality of times. By performing tests with respect to various frequency bands, the reliability of the hearing test may be increased. Also, it may be obvious to one of ordinary skill in the art that operations of the hearing test of the user may be finished after operation 604 according to the user environment.

Embodiments include configurations wherein the processors 140 of the sound source playing apparatus 100 may include an array including a plurality of logic gates, or a combination of a general micro-processor and a memory in which a program that can be executed in the micro-processor is stored.

As described above, the hearing characteristics of a user may be easily tested by the portable sound source playing apparatus 100 and the result of the hearing test may be displayed or reflected in the sound source playing apparatus 100.

In addition, other embodiments of the present invention can also be implemented through computer readable code/instructions in/on a medium, e.g., a computer readable medium, to control at least one processing element to implement any of the above-described embodiments. The medium can correspond to any medium permitting the storage and/or transmission of the computer readable code.

According to the embodiments of the present invention, a hearing test may be easily performed using a portable sound source playing apparatus that performs a hearing ability test using sound speeches that are familiar to a user (examinee). Also, since the portable sound source playing apparatus does not repeatedly play a pure tone, time for testing the hearing ability is reduced and the reliability of the hearing ability test may be increased.

The computer readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as an Internet transmission media. Thus, the medium may be such a defined and measurable structure including or carrying a signal or information, such as a device carrying a bit stream according to one or more embodiments of the present invention. The media may also be a distributed network, so that the computer readable code is stored/transferred and executed in a distributed fashion. Furthermore, the processing element could include a processor or a computer processor, and processing elements may be distributed and/or included in a single device.

It should be understood that the embodiments described therein should be considered in a descriptive sense only and not for purposes of limitation. Descriptions of features or aspects within each embodiment should typically be considered as available for other similar features or aspects in other embodiments.

What is claimed is:

1. A method of testing a hearing ability of a user using a portable sound source playing apparatus, the method comprising:
    extracting at least one phoneme from each of a plurality of groups comprising at least one phoneme each, wherein the plurality of groups are classified based on frequencies of phonemes;
    outputting a signal corresponding to the at least one extracted phoneme;
    obtaining a response of the user regarding a degree of audibility of the output signal;
    determining the degree of audibility of a predetermined frequency band, to which each of the at least one extracted phoneme corresponds, based on the response of the user; and
    measuring hearing characteristics of the user showing the degree of audibility for each frequency band based on a result of determination.

2. The method of claim 1, wherein the determining comprises:
    determining the degree of audibility of a plurality of predetermined frequency bands, based on the response of the user regarding the at least one phoneme included in the plurality of frequency bands corresponding to each of the plurality of groups comprising at least one phoneme each, and
    wherein the measuring comprises:
    measuring the hearing characteristics of the user showing the degree of audibility of each of the plurality of predetermined frequency bands.

3. The method of claim 1, wherein the outputting the signal comprises:
outputting a signal representing a sentence to which at least one method of amplifying a sound source is applied, wherein the obtaining comprises:
obtaining a preference regarding the signal from the user, and
the method further comprises determining a method of amplifying desired by the user, among the at least one method of amplifying a sound source.

4. The method of claim 3, wherein, in the at least one method of amplifying a sound source, a time when compression of the sound source starts is varied.

5. The method of claim 1, further comprising obtaining volume data from the user, wherein the hearing ability of the user is tested using a signal indicating the at least one phoneme at a volume set based on the obtained volume data.

6. The method of claim 1, further comprising displaying a result of testing the hearing of the user according to the hearing characteristics of the user.

7. The method of claim 1, further comprising:
correcting a signal for playing a sound source by applying the hearing characteristics of the user to the signal for playing a sound source, and wherein the outputting includes outputting the corrected signal.

8. The method of claim 7, wherein, the correcting comprises:
applying an amplification gain regarding a frequency of a sound source according to the hearing characteristics of the user and an amplification method desired by the user to correct the signal.

9. The method of claim 1, wherein obtaining the response of the user comprises at least one of recognizing a voice of the user to obtain the response, and obtaining an input signal, which corresponds to the response, input by the user.

10. The method of claim 1, wherein obtaining the response of the user comprises:
obtaining a response of the user regarding the degree of audibility of a sound that is played by another sound source playing apparatus that is connected to the sound source playing apparatus and receives the output signal, and
wherein the determining comprises:
determining the degree of audibility of the predetermined frequency band based on the response of the user regarding the degree of audibility of the sound.

11. A non-transitory computer readable recording medium having embodied thereon a program for executing a method of testing a hearing ability of a user using a portable sound source playing apparatus, the method comprising:
extracting at least one phoneme from each of a plurality of groups comprising at least one phoneme each, wherein the plurality of groups are classified based on frequencies of phonemes;
outputting a signal corresponding to the at least one extracted phoneme;
obtaining a response of the user regarding a degree of audibility of the output signal;
determining the degree of audibility of a predetermined frequency band, to which each of the at least one extracted phoneme corresponds, based on the response of the user; and
measuring hearing characteristics of the user showing the degree of audibility for each frequency band based on a result of determination.

12. A sound source playing apparatus comprising:
a memory which stores a plurality of groups of at least one phoneme which are classified according to a peak frequency of a phoneme which constitutes the at least one phoneme;
an output unit which extracts at least one phoneme from each of a plurality of groups and outputs a signal corresponding to the at least one extracted phoneme;
a user interface unit through which a response of a user regarding a degree of audibility of the output signal is input; and
a processor which determines the degree of audibility of a predetermined frequency band, to which each of the at least one extracted phoneme corresponds, based on the response of the user, and measures characteristics of the user indicating the degree of audibility for each frequency band based on a result of determination.

13. The sound source playing apparatus of claim 12, wherein the processor determines the degree of audibility of a plurality of predetermined frequency bands based on a response of the user regarding syllables included in the predetermined plurality of frequency bands corresponding to each of the plurality of groups, and measures the hearing characteristics showing the degree of audibility of the user with respect to each of the plurality of predetermined frequency bands.

14. The sound source playing apparatus of claim 12, wherein the output unit outputs a signal which represents a sentence to which at least one method of amplifying a sound source is applied, and a preference regarding the signal is input by the user through the user interface unit, and the processor determines the at least one method of amplifying a sound source desired by the user with reference to the input preference of the user.

15. The sound source playing apparatus of claim 14, wherein, in the at least one method of amplifying a sound source, a time when compression of the sound source starts is varied.

16. The sound source playing apparatus of claim 12, wherein the user interface receives volume data from the user, and the processor measures the hearing characteristics of the user using a signal indicating the at least one phoneme at a volume set based on the received volume data.

17. The sound source playing apparatus of claim 12, wherein the user interface unit displays the hearing characteristics of the user.

18. The sound source playing apparatus of claim 12, wherein the processor corrects a signal for playing a sound source by applying the hearing characteristics of the user to the signal, and the output unit outputs the corrected signal.

19. The sound source playing apparatus of claim 18, wherein the processor calculates algorithms for correcting the signal by applying an amplification gain regarding a frequency of a sound source according to the hearing characteristics of the user and the method of amplifying a sound source desired by the user, the memory stores the calculated algorithms, and the output unit outputs the corrected signal which is corrected using the stored algorithms.

20. The sound source playing apparatus of claim 12, further comprising:
an input/output interface which transmits the output signal to another sound source playing apparatus which is connected to the sound source playing apparatus,
wherein the user interface unit obtains a response of the user regarding the degree of audibility of a sound played by the another sound source playing apparatus, and wherein the processor determines the degree of audibility of the predetermined frequency band based on the response of the user regarding the degree of audibility of the sound.

* * * * *